(12) United States Patent
Santamarina et al.

(10) Patent No.: US 7,921,844 B1
(45) Date of Patent: Apr. 12, 2011

(54) BREATH-ACTIVATED FLUIDIC SWITCH AND METHOD FOR DRUG DELIVERY

(75) Inventors: Aland Santamarina, Columbia, MD (US); Ronald D. Stouffer, Silver Spring, MD (US); Russell Hester, Odenton, MD (US)

(73) Assignee: Bowles Fluidics Corporation, Columbia, MD (US)

( * ) Notice: Subject to any disclaimer, the term of this patent is extended or adjusted under 35 U.S.C. 154(b) by 1020 days.

(21) Appl. No.: 11/601,850

(22) Filed: Nov. 20, 2006

Related U.S. Application Data

(60) Provisional application No. 60/739,001, filed on Nov. 23, 2005.

(51) Int. Cl.
*A61M 11/00* (2006.01)
(52) U.S. Cl. .......................... 128/200.18; 128/200.24
(58) Field of Classification Search ............ 128/200.14, 128/200.18, 200.24; 137/803, 804; 239/317, 239/388, 365, 589.1
See application file for complete search history.

(56) References Cited

U.S. PATENT DOCUMENTS

| | | | |
|---|---|---|---|
| 4,278,110 A * | 7/1981 | Price et al. ............... | 137/805 |
| 2006/0213507 A1 * | 9/2006 | Foley et al. ............. | 128/200.14 |
| 2007/0227536 A1 * | 10/2007 | Rivera et al. ............ | 128/200.21 |

* cited by examiner

*Primary Examiner* — Danton DeMille
(74) *Attorney, Agent, or Firm* — Bacon & Thomas, PLLC

(57) ABSTRACT

A drug inhaler of the type having an air jet entraining liquid medicine at an entrainment region from a medicine reservoir and nebulize or atomize entrained liquid by impacting a liquid medicine-laden air jet on a flat surface, and deliver the atomized medicine to a patient via a medicine delivery channel. A breath-activated fluidic switch has a power nozzle coupled to a source of air under pressure. The fluidic breath-activated switch has a pair of diverging legs, one of the diverging legs has a control port connected to sense inhalation of the patient, the other of the legs is coupled to the medicine entrainment region, whereby the entrainment of medicine at the medicine entrainment region is prevented by air supplied to the medicine entrainment region from the other of the legs in the absence of sensed patient inhalation at the control port. The fluidic control port is located downstream of the power nozzle a predetermined distance downstream of the wall attachment point.

5 Claims, 1 Drawing Sheet

BREATH-ACTIVATED FLUIDIC SWITCH AND METHOD FOR DRUG DELIVERY

REFERENCE TO RELATED APPLICATION

The present invention is the subject of provisional application Ser. No. 60/739,001 filed Nov. 23, 2005 for which priority is claimed.

BACKGROUND AND BRIEF DESCRIPTION OF THE INVENTION

This invention pertains to a class of drug inhalers that uses an air jet to first entrain liquid medicine and then nebulize or atomize the liquid by impacting the medicine-laden air jet on a flat surface. This aerosol is then inhaled by the patient.

It is an object of the invention to provide a breath-activated fluidic switch and method for shutting off the medicine when the patient is not inhaling, whether he is exhaling or has removed the drug delivery device from its position of inhaling.

According to the invention, a fluidic switch is provided for a drug inhaler which uses an air jet to first entrain liquid medicine, then nebulize or atomize the liquid by impacting the medicine-laden air jet on a flat surface. A fluidic switch turns on and off the entrainment of liquid medicine. A feature of the invention is that the fluidic control port is not mounted at the traditional position at the exit of the power nozzle but is downstream thereof and preferably by approximately three nozzle widths.

BRIEF DESCRIPTION OF THE DRAWINGS

The above and other objects, advantages and features of the invention will become more apparent when considered with the accompanying specification and attached drawings wherein.

DETAILED DESCRIPTION OF THE INVENTION

Figure 1:
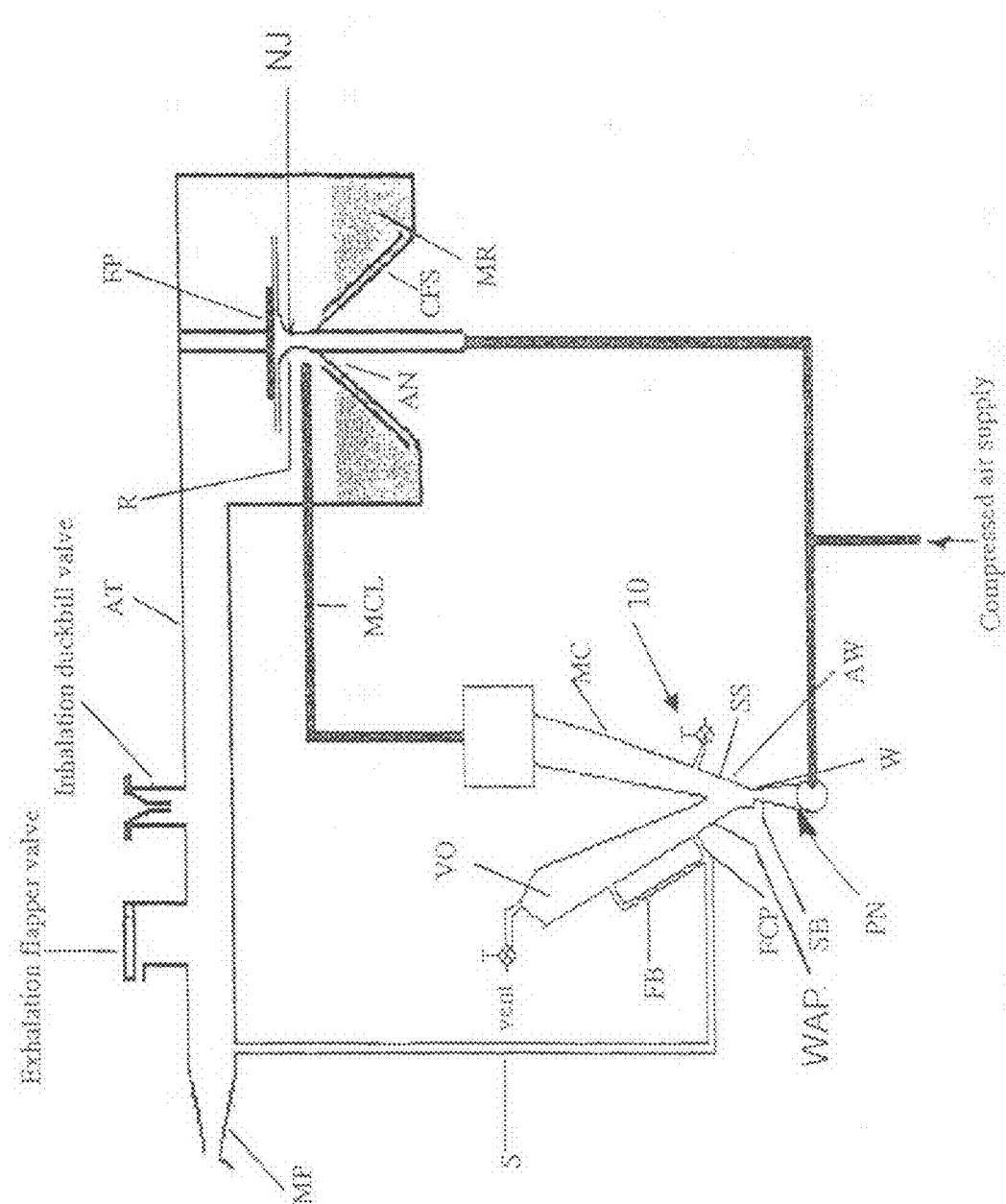
FIG. 1 is a schematic drawing showing the entire inhaler system including a breath operated fluidic medicine cut-off device incorporating the invention.

Referring to the drawing, the known or prior art portion of the drug inhaler includes a medicine reservoir MR having a conical feed surface CFS with an air nozzle AN coupled to a compressed air supply. The compressed air jet NJ entrains liquid medicine from the supply MR and, then the entrained liquid medicine impacts or impinges on the flat plate FP to atomize or nebulize the medicine. This aerosol is inhaled through an aerosol tube or channel AT to the patient outlet or delivery point. The aerosol tube AT is provided with an inhalation duck bill valve and an exhalation flapper valve which operate in conventional fashion.

THE PRESENT INVENTION

As shown in the drawing, a separate fluidic switch 10 is incorporated to switch additional air via medicine control line MCL into the medicine control region R where the medicine is being entrained. The additional air satisfies the entrainment requirement of the main nebulizing jet NJ and therefore stops the flow of medicine. The medicine is stopped at anytime the patient is not inhaling.

The fluidic element 10 employed behaves as a logical NOR element. It is purposely biased to the medicine control line MCL (medicine cutoff) in the absence of an input signal. The input signal S is from the inhalation which drops from near atmospheric to a vacuum of under 2.5 cm $H_2O$ at onset of inhalation by the patient. This small vacuum switches the fluidic element from the medicine control leg MC to the vented output leg VO, thereby removing the medicine-stopping air jet from the medicine control line MCL so that normal nebulizing may proceed during the inhalation phase of the breathing cycle. Whenever the patient is not inhaling, the device pressure is nearly atmospheric (even when the device is removed or not in use) so that the fluidic element 10 switches to the air output going to the medicine control leg MC and medicine control line MCL to turn off the medicine flow.

Fluidic Control Port (FCP)

Notice the FCP is not at the traditional position at the exit of the power nozzle PN, but downstream by about three power nozzle widths. This position is just downstream of the wall attachment point WAP. If the traditional upstream position were to be used, the vacuum produced by the proximate power jet would be many times the patient produced vacuum of a couple centimeters of water.

Bias to the Medicine Control (MC)

The proper bias to the medicine control leg MC in absence of an input signal is achieved by the cooperative effect of four geometrical adjustments.
 1. Use feedback FB on the vent side VO
 2. Incorporating a setback SB in a portion of the vent-side attachment wall.
 3. No setback on medicine control leg MC side attachment wall SS.
 4. Decrease attachment wall AW angle on medicine control leg MC side.

Design modifications 1 and 2 decrease the attachment on the vent side while design modifications 3 and 4 increase the attachment on the sleeve or medicine control leg MC side. Fluidic element can be designed to be sensitive enough for the use by an infant or seriously ill patient. These patients tend to produce weaker input signals.

While the invention has been described in relation to preferred embodiments of the invention, it will be appreciated that other embodiments, adaptations and modifications of the invention will be apparent to those skilled in the art.

What is claimed is:

1. In a drug delivery device of the type having an air jet entrained liquid medicine at an entrainment region from a medicine reservoir and nebulized or atomized entrained liquid by impacting a liquid medicine-laden air jet on a flat surface, and delivering the atomized medicine to a patient via a medicine delivery channel, the improvement comprising:
 a breath-activated fluidic switch having a power nozzle coupled to a source of air under pressure, said breath-activated fluidic switch having a pair of diverging legs, one of said diverging legs having a control port connected to sense inhalation of the patient, the other of said legs being coupled to said medicine entrainment region, whereby said entrainment of medicine at said medicine entrainment region is prevented by air supplied to said medicine entrainment region from said other of said legs in the absence of sensed patient inhalation at said control port.

2. The invention defined in claim 1, wherein said fluidic control port is located downstream of said power nozzle a predetermined distance downstream of a wall attachment point.

3. The invention defined in claim 1, wherein said power nozzle has a width (W) and said control port is located about three times the width (W) from said power nozzle.

4. The invention defined in claim 1, wherein said one of said diverging legs having a control port includes a feedback from a point downstream of said control port to said control port, and said one of said diverging legs having said control port having a setback adjacent said power nozzle.

5. The invention defined in claim 1, wherein a bias to the medicine control in the absence of sensed patient inhalation is achieved by one or more of the following geometric adjustments:

a use feedback (FB) on the vent side (VO);
a setback (SB) incorporated in a portion of the vent-side attachment wall;
the (MC) side attachment wall (SS) is not setback; and
the attachment wall (AW) angle on the medicine control (MC) side is decreased.

\* \* \* \* \*